United States Patent [19]

Sodickson et al.

[11] 4,298,345

[45] Nov. 3, 1981

[54] METHOD AND APPARATUS FOR CHEMICAL SPOT TEST ANALYSIS

[75] Inventors: Lester A. Sodickson, Newton, Mass.; Franklin Lim, Richmond, Va.

[73] Assignee: Damon Corporation, Needham Heights, Mass.

[21] Appl. No.: 25,497

[22] Filed: Mar. 30, 1979

Related U.S. Application Data

[62] Division of Ser. No. 853,435, Nov. 21, 1977, Pat. No. 4,178,153.

[51] Int. Cl.$^3$ .................. G01N 1/14; G01N 21/27
[52] U.S. Cl. .................. 23/230 R; 422/56; 422/100
[58] Field of Search .......... 23/230 R; 422/56, 57, 422/58, 100

[56] References Cited

U.S. PATENT DOCUMENTS

| | | |
|---|---|---|
| Re. 28,339 | 2/1975 | Maxon . |
| 2,812,243 | 11/1957 | Goody . |
| 3,138,015 | 6/1964 | Avery .................. 210/387 |
| 3,245,306 | 4/1966 | Potter et al. .................. 356/210 |
| 3,526,480 | 9/1970 | Findl et al. . |
| 3,549,328 | 12/1970 | Kilburn .................. 23/230 R X |
| 3,907,503 | 9/1975 | Betts et al. .................. 23/230 R X |
| 3,937,614 | 2/1976 | Sodickson et al. . |
| 3,992,158 | 11/1976 | Przbylowicz et al. .................. 422/57 |
| 4,023,930 | 5/1977 | Blunck et al. . |
| 4,046,513 | 9/1977 | Johnson . |

FOREIGN PATENT DOCUMENTS

| | | |
|---|---|---|
| 441347 | 11/1934 | United Kingdom . |
| 602470 | 5/1945 | United Kingdom . |
| 806928 | 3/1956 | United Kingdom . |
| 1218749 | 12/1967 | United Kingdom . |
| 1281818 | 10/1970 | United Kingdom . |
| 1365001 | 2/1972 | United Kingdom . |
| 1365651 | 2/1973 | United Kingdom . |
| 1432811 | 4/1973 | United Kingdom . |
| 1435400 | 11/1974 | United Kingdom . |
| 1522965 | 8/1975 | United Kingdom . |
| 1547846 | 10/1976 | United Kingdom . |

OTHER PUBLICATIONS

Klaus, "Critical Layers on Photometric Evaluation of Thin Layer Plates," Journ. of Chromatography, vol. 16:311-326, 1964.

Primary Examiner—R. E. Serwin
Attorney, Agent, or Firm—Kenway & Jenney

[57] ABSTRACT

Chemical analysis of a sample with reagents spotted on a fibrous or porous medium employs a medium pretreated both with reagents and with conditioning agent. The conditioning agent increases the degree to which the liquid reactants wet the medium. One form of pretreated medium has different reagents located predominantly within different selected zones.

Liquid is applied to the medium, typically as diluted sample, at a rate selected to enhance formation of repeatable spots. In one embodiment the liquid is applied by flowing it onto a wick element seated on the medium. The wick is disc-like and small relative to the spot which the reactants form on the medium. The disc can be pretreated to carry reagent, which the liquid transfers to the medium.

The analysis instrument receives a reaction medium between selectively recessed upper and lower surfaces aligned in opposition at the reaction spot being analyzed.

The analysis can, depending on the analytical reaction, the medium and the precision required, proceed while the reactants are wet or can measure a reaction product after the reactants are dry. A single point analysis can also be made.

15 Claims, 9 Drawing Figures

METHOD AND APPARATUS FOR CHEMICAL SPOT TEST ANALYSIS

This is a division of application Ser. No. 853,435, filed Nov. 21, 1977, now U.S. Pat. No. 4,178,153.

BACKGROUND

This invention relates to improvements in the method and apparatus for analysis of constituents carried in a fibrous or porous medium set forth in the commonly-assigned and copending U.S. Pat. No. 4,059,405, issued Nov. 22, 1977. The disclosure of that patent is incorporated herein by this reference. The referenced patent issued on Application Ser. No. 715,855, which is a continuation-in-part of abandoned copending Application Ser. No. 498,646 for "Method And Apparatus For Analysis Of Constituent Carried In Fibrous Medium" filed Aug. 19, 1974; which is a continuation-in-part of the abandoned copending Application Ser. No. 243,068 for "Method For Constituent Analysis With Thin-Layer Reactant Mixture" filed Apr. 11, 1972.

A general object of this invention is to provide improved articles and compositions, and improved methods, for chemical spot test analysis, with an optically thin concentration of a measured reaction product, which enhance the precision of analysis, which facilitate performing the analysis, and which expand the uses of such analysis.

One specific object of the invention is to provide improvement of a fibrous or other porous medium for use in chemical spot test analysis and which is pretreated to bear at least some reagent for producing the reaction product of measurement with an optically thin concentration.

Another specific object of the invention is to provide a disposable article for enhancing the delivery of liquid to a reaction medium for use in chemical spot test analysis of the above character.

A further feature of the invention is to provide improved instrument structure for enhancing the repeatability and precision of chemical spot test analysis measurements with an optically thin concentration of the measured reaction product.

Other objects of the invention will in part be obvious and will appear hereinafter.

SUMMARY OF THE INVENTION

According to the invention, chemical spot test analysis with an optically thin concentration of measured reaction product is carried out with a fibrous or other porous medium pretreated with agent that conditions the medium for enhanced containment of liquid reactants. The conditioning agent thus increases the degree to which liquid reactants wet the medium at a spot-like reaction site. The pretreatment of the medium preferably also introduces at least some reagents. Thus, in a typical instance, a pretreated medium which appears simply as a dry strip of paper is put to use simply by addition of the sample to be analyzed with sufficient liquid to fluidize the reactants at a selected site. The pretreatment of the medium with reagents and with conditioning agent generally is confined to the reaction sites for reasons of economy and convenience.

The conditioning agent increases the liquid-holding capacity of the medium to contain reactants at the site in a liquid state without undue spreading. The agent thus conditions the medium to have a liquid absorption characteristic such that liquid reactants come to rest at a higher fluid content per unit area of the medium, but below the saturation level, than would occur without such agents. The attainment of this high degree of wetness at the reaction site contains a given liquid volume in a smaller spot than would otherwise occur, and it enhances the precision of the analytical measurement.

Useful conditioning agents appear to have a balance of hydrophobic and hydrophilic molecules, either individually or as part of a polymer. The hydrophobic portion presumably serves to repel fluid from the particles of fibers of the medium, and the hydrophilic portion presumably serves to facilitate entry of liquid into the interstices of the medium. A typical conditioning agent includes a thickening agent and a surfactant. Suitable thickening conditioning agents are polyox (as set forth in the referenced U.S. Pat. No. 4,059,405 at [Application Ser. No. 715,855 at pages 48-49] ), albumin, gum arabic, guar gum, and mannitol. Suitable surfactants can be selected from those available and by way of example include Brij. The low molecular weight polyol surfactants marketed by the BASF Corporation under the trade designations Pluronic and Tetronic have also been successfully used as conditioning agents. These are available in numerous polymeric forms with varied ratios of hydrophobic and hydrophilic portions.

The foregoing use of conditioning agent is considered advantageous at least in part due to the finding that measurements on reactive liquids during the production of reaction product are preferably made with a selected range of wetness within the structure of the reaction medium. Such measures attain higher precision than other conditions of wetness. The conditioning agent of this invention enhances the attainment of the desired relatively high and stable wetness condition during measurement.

In a preferred practice of the invention, the conditioning agent is blended in liquid form with at least some of the reactants for the prescribed analytical reaction. The resultant liquid reagent system is applied to a fibrous sheet such as Schleicher & Schuell type 903-C test paper. The resultant pretreated sheet, which after drying has a significant shelf life, is put to use for a spot test analysis, for example of blood serum, by depositing diluted serum, and whatever further reagents the analysis requires, on a pretreated site of the sheet. The resultant reaction is monitored, typically with a fluorometer or other form of photometer, to measure the selected constituent-manifesting reaction product.

In further practice of the invention, the reaction medium is prepared with reagents, as well as with conditioning agent as desired, in a manner that applies different reagents within different zones of each site. This zoned introduction of reagents is used, for example, where different reagents are to be substantially isolated from one another until initiation of the analysis reaction, or simply to control the reagent physical distribution. Different reagents can be zoned in accordance with the invention by first depositing in liquid form one or more reagents that are stable together, together with conditioning agent as suitable, to the center of a reaction site and allowing the solution to spread. This is followed by deposition at the center of the site of a selected volume of water or other liquid to wash the previously applied reagent outward from the center of the site. Thereafter, and typically after drying the medium, the further reagent is deposited at the center of the site with sufficiently small liquid volume so as not to spread beyond the previously-depleted central region. After drying, the medium with reagents zoned to different portions of each site in this manner can be stored until use in the same manner as noted above. Where reagents are to be zoned but without such high isolation, the wash step can be omitted. The first deposition of reagent, however, is generally dried before applying the second reagent.

A sample is analyzed on a pretreated medium by introducing the sample and liquid to a reaction site, and by monitoring the resultant constituent manifesting reaction. The liquid required for fluidizing the reactants typically is introduced with the sample as a diluent. Where the medium is a fibrous paper-like sheet, as well as with other structures of porous medium, it is advantageous to deliver the liquid at a controlled rate. It has been found that too slow a delivery of liquid tends to deplete the center of the site of reagent constituents, whereas delivering liquid too rapidly results in irregular and hence non-repeatable spot formation. In one preferred practice of the invention, an optimum liquid delivery rate with a pipette forms a steady but small and stable pool of liquid on the medium beneath the pipette tip. The optimum rate maintains this pool, i.e. fresh liquid is delivered at essentially the same rate at which the medium draws liquid from the pool. Disappearance of the pool denotes too slow a rate of liquid delivery, and too rapid a delivery causes the pool to become unstable so that liquid spills outward from the pool and flows over the top of the medium.

The invention facilitates controlling the delivery of sample liquid to a reaction medium site at the desired rate by providing a wick-like fluid delivery-controlling element seated on the center of the site and through which the liquid is delivered. The wick element preferably is in the form of a cylindrical disc. It is significantly smaller than the spot which the reactants form at the site, and hence covers only the central portion. For example, a cylindrical wicking disc of between 1½ and three millimeter diameter has been found successful; in that instance the reactants formed a spot of roughly ten millimeter diameter. The disc is of fibrous or other porous structure; typically it can be punched from the same kind of sheet used as a reaction medium. In operation, the disc is placed at the center of the reaction site and the diluted sample or other liquid is applied directly to it. The liquid enters the reaction medium from the disc. The wicking disc apparently provides a buffering capacity for excess liquid, and appears artificially to create a liquid delivery zone similar to the small puddling or pool noted above as desirable for direct application of liquid to the medium. The disc is readily removed from a reaction site after delivery of liquid through it and before commencing measurement. Alternatively, the measuring instrument can accommodate the disc. Another suitable wicking element is of porous hydrophilic polyethylene.

The wicking disc can be pretreated with reagent for introducing the reagent to the reaction site together with the sample or other liquid. The delivery of a reagent in this manner is often advantageous, as where it is unstable in the presence of other reagents or otherwise is to be maintained separate from other reactants prior to commencement of the reaction. The pretreatment of the disc with a reagent involves absorbing a liquid solution or a suspension of the selected reagent in the disc, and drying the disc, and where applicable packaging it to preserve the reagent. Delivering liquid to a reaction site through such a pretreated disc automatically washes the reagent from the disc onto the site. This introduces the disc-carried reagent to the other reagents at the desired time and, further, with the desired controlled rate of liquid delivery.

Alternative to making measurement when reactants are wet, the invention can be practiced, at least with some analysis chemistries, with a measurement of reaction product when the reactant spot is dry. Further, the invention in some instances can be practiced, albeit with some loss of precision, with a single point measurement, i.e. with a single measurement of reaction product. A single measurement can be made upon substantial completion of the constituent manifesting reaction, or thereafter when the reactants are dry. The basis for the single point measurement of reaction product present in optically thin concentration is that the signal of interest is sufficiently distinguished from fluctuations in the background characteristics of the medium and of the reactants. This large manifestation of the reaction product relative to background and other non-repeatable signals results from improved chemistries for producing the reaction product and from improved procedures which diminish the fluctuations of the background signal. With these practices, the analysis with single-point measurement can yield precision of at least five percent.

The invention also features improvements in a photometric instrument for performing spot test measurements with optically thin concentrations of reaction product. The instrument disposes the reaction medium in the path of optical energy between a source and a detector by seating it between an optical window and an opposed surface which is either a second optical window or a surface of other selected optical character, e.g. of selected reflectivity. In either event, both surfaces which face the reaction site are closely but measurably recessed from the medium. The intervening recess spaces preferably are sufficient to avoid physical contact between the medium and the surface under all normal conditions of wetness. It has been found that this condition enhances the repeatability and uniformity of optical coupling with the medium.

The invention accordingly comprises the several steps and the relation of one or more of such steps with respect to each of the others, apparatus embodying features of construction, combinations and arrangements of parts adapted to effect such steps, and articles which possess characteristics, properties and relations of elements, all as exemplified in this disclosure, and the scope of the invention is indicated in the claims.

BRIEF DESCRIPTION OF DRAWINGS

For a fuller understanding of the nature and objects of the invention, reference should be made to the following detailed description and the accompanying drawings, in which.

DESCRIPTION OF ILLUSTRATED EMBODIMENTS

Figure 1:
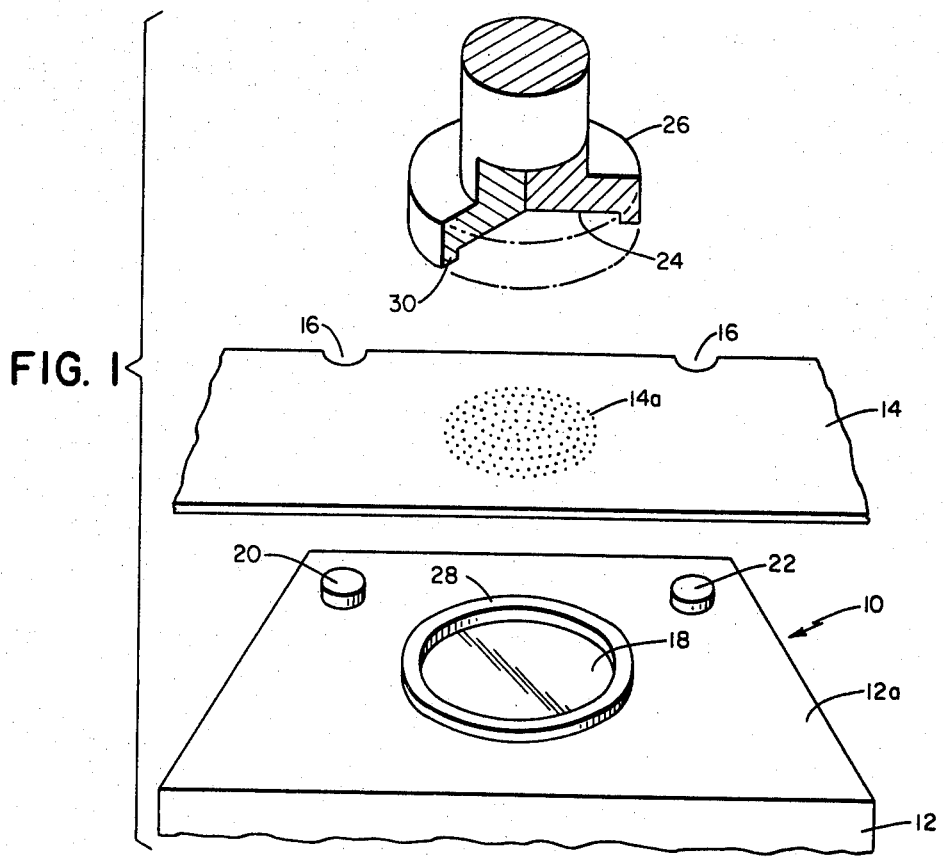
FIG. 1 is a simplified showing of a fragment of an instrument for practicing the invention.

FIG. 1 shows an optical instrument 10 for performing chemical spot test analysis and illustrating improvements which the invention provides over the instruments which the referenced U.S. Pat. No. 4,059,405 patent describes. The illustrated instrument has a body 12 with a top panel 12a that receives a sheet-like fibrous reaction medium 14 for the measurement of a reaction product at a reaction site 14a of the sheet. The fibrous sheet 14 typically is a strip having numerous reaction sites spaced apart from one another and aligned in a row. The strip is recessed along one longitudinal edge, illustrated as the back edge, with positioning notches 16. In the illustrated arrangement there is one such notch 16 longitudinally interposed between every two adjacent sites 14a. An optical window 18 in the top panel of the instrument enables optical elements within the instrument to direct electromagnetic energy onto the reaction site 14a, and enables further optical elements within the instrument housing to receive resultant electromagnetic radiation, e.g. reflected at the wavelength of illumination or fluorescence.

Two particular features of the instrument 10 are sheet-aligning pins 20 and 22 on the panel 12a, and a recessed surface 24 in the instrument backing head 26 that seats on the fibrous sheet 14 above the optical window 18. The two pins 20, 22 are selectively located on the housing panel 12a relative to the optical window 18. The geometry is such that a reaction site 14a is located in optical alignment directly above the window 18 when the notches 16 are seated on the two pins 20 and 22. The pins thus locate the fibrous sheet along both lateral axes of the sheet to locate a reaction site in the proper measuring position relative to the instrument window 18.

As the referenced patent sets forth, the exterior upper surface of the optical window 18 is recessed to diminish the likelihood that it engages the fibrous sheet 14. This can be done by recessing the window below the upper surface of the top panel 12a, or by providing a cylindrical rim 28, as illustrated, which projects upward on the top panel beyond the window 18. In addition, the instrument 10 has a backing head 26, typically mounted on the instrument with a hinged or jointed structure to allow the head to be raised away from the top panel and alternatively be lowered to engage the fibrous sheet 14 opposite the window 18. In accordance with the invention, the backing head has a flat surface 24 which overlies the sheet 14 directly in register above the window 18 and is recessed away from the sheet. In the operative position shown in FIG. 2, backing the surface 24 is parallel with the window 18. A projecting cylindrical rim 30 on the backing head extends beyond the surface 24 toward the housing panel 12a to engage the fibrous sheet in opposed registration with the periphery of the window 18, i.e. in the illustrated embodiment to bear against and engage the sheet directly opposite the cylindrical rim 28.

Figure 2:
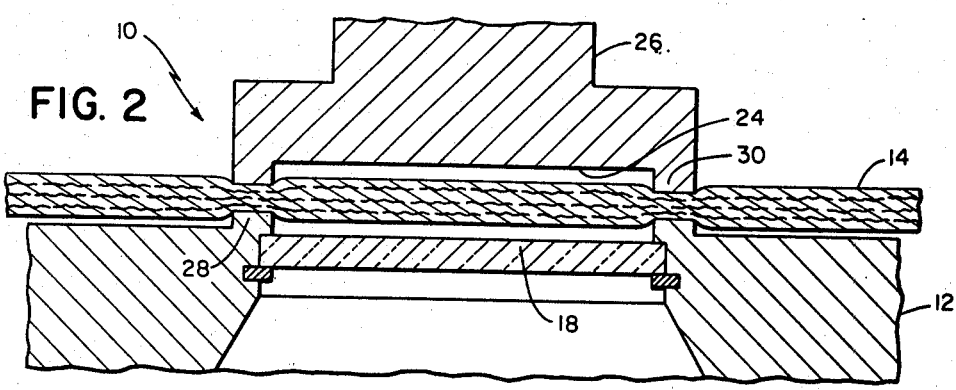
FIG. 2 is a side elevation view of the instrumental apparatus of FIG. 1 in use.

With this construction shown in FIGS. 1 and 2, the instrument 10 positively locates a reagent sheet for repeatable, precise measurements. The instrument lightly clamps the sheet at the periphery of the monitored spot-like area which is in the instrument field of view. This clamping, which the illustrated construction effects by the opposed rims 28 and 30, retards the loss of liquid, e.g. by evaporation, absorption or other transfer, from the monitored area, and it securely seats the sheet at a fixed space relative to the optical window 18 and to the backing surface 24. The spacings of the sheet from the recessed window 28, and from the recessed surface 24, avoid contact of the sheet with either surface, and this has been found to enhance the repeatability of the coupling of optical energy between the instrument and the fibrous sheet. It will be appreciated that the backing surface 24 can be the surface of an optical window of the instrument 10, and generally has a selected optical reflectance, absorbance or other character. Further, the internal optical system of the instrument generally includes elements which select the field of view, which typically ranges from between six and ten millimeters in diameter, with eight millimeters preferred for the example set forth hereinbelow. Alternatively, a thin opaque sheet with an aperture can be placed over the window 18 to define the field of view.

By way of illustrative example, an instrument 10 as shown having an eight millimeter field of view has an optical window of 12.5 millimeters diameter recessed by 0.25 millimeters below the plane at which the lower surface of the sheet is clamped (e.g. below the outer face of rim 28), and has a flat circular surface 24 of like diameter and like recess from the outer face of rim 30. The raised tim is typically 1–2 mm wide.

Figure 3:
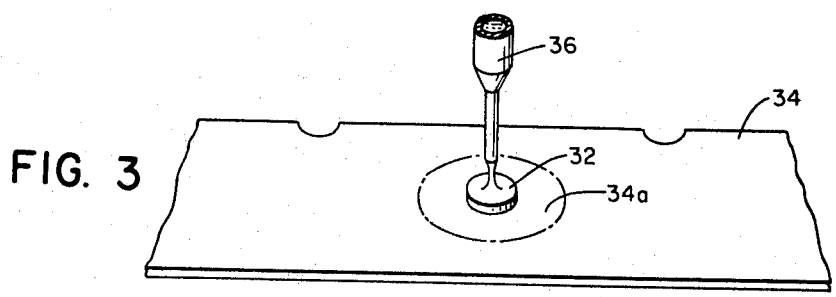
FIG. 3 shows a sheet-like medium and wicking disc in accordance with features of the invention.

Examples set forth below illustrate chemical spot tests analysis with an initially dry medium pretreated with reagents so that the introduction of a diluted sample initiates the analytical reaction. To facilitate this introduction of liquid to the medium at a selected rate, as discussed above, the invention features the use of a small wicking disc 32, as FIG. 3 illustrates. The disc is placed directly on a reaction medium 34 at the center of the reaction site 34a at which an analysis is to be carried out. The liquid to be delivered to the site to initiate or carry out the analysis is applied to the disc, rather than to the medium, and the disc transfers the liquid to the reaction site at the desired selected rate. FIG. 3 shows the delivery of liquid by way of a pipette, of which only the tip 36 is shown, onto the top of a cylindrical disc 32. The disc 32 controls the transfer of liquid as described previously, and thereby facilitates the desired delivery of liquid by relatively unskilled technicians and without elaborate pipetting equipment.

EXAMPLE 1

Glucose End-Point Assay

A first example provides a glucose reagent system illustrating several features of the invention. One feature is use of the system for an end point assay, more particularly an assay made with at least two measurements at a single reaction site, one prior to production of the reaction product and the other upon completion (i.e. at the end point) of the product-producing reaction. The reagent system is prepared as a blend of the following ingredients:

TABLE I

| | GLUCOSE REAGENT | |
|---|---|---|
| Constituent | Concentration (Quantity/ml) | Commercial Designation |
| TRIS-Cl | 0.563 m (milli) moles | Sigma #T-3253 |
| TRIS Base | 0.437 m moles | Sigma #T-1503 |
| Succinic Acid | 0.017 m moles | Sigma #S-7501 |
| NaHCO$_3$ | 0.024 m moles | Baker #3506 |
| MgCL$_2$ | 0.039 m moles | Sigma #M-0250 |
| Adenosine Triphosphate | 0.033 m moles | Sigma #A-3127 |

TABLE I-continued

GLUCOSE REAGENT

| Constituent | Concentration (Quantity/ml) | Commercial Designation |
| --- | --- | --- |
| (ATP) Nicotinamide-adenine-dinucleotide-phosphate (NADP) | 0.034 m moles | Sigma #N-0505 |
| Serum Albumin, Bovine | 0.513 g % (W/V) | Sigma #A-4378 |
| Glucose-6-phosphate dehydrogenase (G-6-PDH) | 20.5 IU (International Units) | Sigma #G-6378 |
| Hexokinase | 25.6 IU (International Units) | Sigma #H-4502 |
| Brij-35 | 0.03% (W/V) | Sigma #430 AG6 |

Features of this reagent system include relatively high concentrations of ATP and of NADP, and the inclusion of albumin, here in the form of bovine serum albumin, together with a trace of surfactant, here Brij-35. The reagent system thus includes both reagents for carrying out the assay, and conditioning agents for treating the medium and including both thickening agent and surfactant. The surfactant of the conditioning agent is understood to enhance the absorption by the reaction site of the diluted sample. Without it, the solution appears to take longer to enter the medium, and tends to form irregular spots. Reaction sites are prepared with this reagent system by depositing twenty-five microliters of the liquid composition on dry, unbounded type 903-C paper. The treated paper is dried in a dessicator to constant weight under vacuum, and is sealed in foil packages. The resultant reagent sites are stable for at least six months when stored frozen, and for at least three months when stored at room temperature.

To perform a glucose-assaying measurement, a fresh reaction site is placed over the window of a fluorometer constructed as shown in the referenced patent with the improvements of FIGS. 1 and 2. The fluorometric analysis instrument illuminates the reaction site with excitation at 340 nm, and measures fluoresence at 460 nm. A sample of blood serum is diluted 1:25 in water containing 1% (V/V) of Brij-35 (30% solution). Twelve microliters of the dilution are applied to each reaction site at a controlled rate of delivery, for the reasons and in the manner set forth above. The diluted sample accordingly is applied with a pipette at a controlled rate that maintains at the reaction site center a visible liquid pool of one to two millimeters diameter. For this operation, the twelve microliters typically are applied in 0.5 to 1 second. Alternatively, the reagent system can be applied using a wicking disc as descrived above with reference to FIG. 3.

The reaction commences substantially upon deposition of the diluted serum, and proceeds to completion in approximately two minutes. This is significantly faster than the glucose reaction described in the U.S. Pat. No. 4,059,405 patent. It is understood that the reason for this increased rate of reaction is that the reaction site has a higher concentration of liquid, i.e. is wetter, due to the deposition of conditioning agent at each site. A measure of the precision attained with this reaction system and procedure is set forth in Table II, which tabulates measurements from six replicate samples of a mid-range blood plasma pool having a glucose concentration of 110 milligrams per deciliter (mg/dl). The fluorescence measured at each spot, i.e. for each sample, initially falls from the relatively high background value of the dry medium as the sample is added, and has a minimum value at approximately six seconds after initiation of the reaction. It attains a maximum value, corresponding to completion of the reaction, within two minutes.

TABLE II

| Spot # | Minimum Reading* | Maximum Reading* | Difference |
| --- | --- | --- | --- |
| 1 | 1.05 | 2.77 | 1.72 |
| 2 | 1.12 | 2.87 | 1.75 |
| 3 | 1.11 | 2.86 | 1.75 |
| 4 | 1.37 | 3.16 | 1.79 |
| 5 | 1.22 | 3.01 | 1.77 |
| 6 | 1.16 | 2.93 | 1.76 |
| mean | 1.17 | 2.93 | 1.76 |
| std. dev.* | 0.112 | 0.137 | 0.027 |
| std. dev. (mg/dl) | 7.5 | 9.1 | 1.8 |
| mean (mg/dl) | | | 110 |

Table II sets forth that, when the difference between the minimum and the maximum fluorescent signal readings are used as the measure of the signal, the standard deviation for the six replicates is 1.8 milligrams per deciliter. By contrast, the standard deviations of the maximum readings and of the minimum readings, are 7.5 and 9.1 milligrams per deciliter, respectively, which is significantly higher. Standard curves derived by plotting the observed differences as a function of glucose concentrations are linear from 0 to 300 milligrams per deciliter, with correlation coefficients typically of 0.98 or higher. Correlation studies with routine methods for fifty-nine specimens ranging in value from 50 to 400 mg/dl of glucose showed excellent agreement, with a correlation coefficient of 0.989. Specimens above 300 mg/dl are re-run at higher dilution to maintain linearity.

It is expected that the system will yield equivalent results at higher dilution (e.g. 1:50) when operated on another medium such as Whatman No. 3, which has a comparable effective pathlength and approximately one-half the flourescent background as the 903-C paper. Under such improved conditions, the linear range will be extended to 600 mg/dl.

The inclusion of conditioning agent with albumin or other thickening agent in the glucose reagent system of Table I, as well as in numerous other reagent systems for spot analysis has been found to be advantageous to stabilize the reagent for extended storage, and to reduce the capillary spreading of the reagent liquid on the reaction medium. It appears that polyox, albumin and other thickening agents can be used interchangeably, and can be provided as a matter of convenience either in the reagent system itself or as a separate pre-reagent treatment of the reaction medium. The important consideration appears to be that the reaction mixture comes to rest within a smaller diameter on the medium with an increased localized liquid concentration, as contrasted to instances lacking conditioning agents. These changes in turn are observed to provide greater stability in the effective optical pathlength, with the net result of an enhanced measuring precision.

It has, however, been observed that the fluorescence measured using the foregoing glucose system exhibits a slight increase with time, and that the rate of variation is similar both with and without glucose present in the reaction medium. This increase is considered to result from a gradual loss of fluid from the monitored eight millimeter diameter field of view, due to spreading of the liquid to a ten to twelve millimeter diameter extent, and due to other fluid losss mechanisms such as evaporation. These fluid loss mechanisms reduce the wetness of the paper, i.e. it gradually dries. The transfer of liquid from the eight millimeter field of view to the contiguous annular zone of the medium is considered advantageous because it allows the reaction site to select the volume of liquid with consequent reduced dependence on the actual volume deposited. Another advantage is that the most non-uniform "ringing" can be outside the field of view.

EXAMPLE II

Glucose Single Point Assay

The repeatability of maximum readings with Example I is limited by spot-to-spot variations in the background fluorescence level of the 903-C paper used as the reaction medium. Other suitable reaction media, have been found, however, such as Whatman paper #3 and S&S paper #2316 and #2040B, which have background fluorescence levels approximately one-half that of the 903-C paper. Yet the latter fibrous media exhibit effective optical pathlengths, from multiple optical scattering interactions with the fibers, roughly the same as for 903-C paper. Consequently, by performing the glucose assay of Example I on these alternate papers, one can reduce the spot-to-spot variations to a level below five percent of the reaction-produced change, so that the maximum reading alone may be used. This technique can yield a single point measurement taken after completion of the reaction which produces the reaction product being measured. The measurements on different samples are, of course, made under the same condition for which the assay is calibrated, e.g. at a specified time after commencement of the reaction. As this condition of measurement is increasingly delayed beyond start of the reaction, so that the optical pathlength at the monitored site increases, the reaction is performed with an increasingly diluted sample in order to maintain the optically-thin condition across the instrument field of view.

To demonstrate the technique, the Eskalab Glucose tablet (marketed by Smith, Kline and French) was made up in one-fifth its usual liquid volume by dissolving one tablet in 0.6 microliters of deionized water. Fifteen microliters of the reagent solution prepared in this manner were applied to each site on S&S #2316 filter paper and allowed to dry. The inert binder of the tablet appeared to function on this paper medium similar to the thickening element of a conditioning agent. The sample and the standards were diluted 1:50 in deionized water and applied in sequence to the sites. These were then covered for fifteen minutes to limit evaporation while the reaction took place, and then opened to the air to dry; this procedure is considered to ensure that the several sites dried equally. The absolute fluorescence levels of the monitored eight millimeter portions of the sample spots were compared with the corresponding levels produced on other sites by standard analysis solutions. The instrument operated with the same 340 and 460 wavelengths as in Example I, but responded to fluorescence emission transmitted through the filter paper in the manner described with reference to FIG. 7 of the referenced patent.

The results showed a standard curve linear to 200 mg/dl glucose concentration. Eight replicates of a 100 mg/dl standard gave a standard deviation of 3.4 mg/dl. At the same time, the measurement of the dry fluorescence of thirty-six reagent-containing spots showed a standard deviation, expressed in clinical units, of about 1 mg/dl, which is roughly one-third of the total. The latter precision is a fixed error independent of glucose level. The 3.4 mg/dl error is a composite of this fixed error and of a proportional error which adds as the square root of the sum of squares. Thus the anticipated proportional error is $(3.4^2-1^2)^{\frac{1}{2}} = 3.25$ mg/dl, or 3.25% of the glucose concentration. When the dilutions are increased to 1:100, the fixed error increases to 2%, and when combined with the 3.25% proportional error still yield a composite precision of about 4% at the 100 mg/dl level. The linear range of the assay then extends to 400 mg/dl. As in Example I, the buffer zone of the reaction medium beyond the monitored areas desensitizes the results from variations in the volume of the diluted sample applied to the site.

These results demonstrate that quantitative measures can be obtained with a reagent system which is optically thin to minimize the effects of "ringing", and yet which is sufficiently concentrated to produce changes which are large compared to the spot-to-spot variation of the selected background.

It has also been found that the same dry spots can be measured with an instrument that responds to the reflected 340 nm energy. As expected for the optically thin condition, the reflected 340 nm signal shows a linear decrease with increasing Glucose level, and it correlates well with the linear increase observed in fluorescence. The precision appears to be roughly double that observed in fluorescence when corrected to the 100 mg/dl level.

The utility of the foregoing technique as well as of all the cited Examples of chemical spot test analysis in evidence with this invention, can be extended by use of other porous media with lower fluorescence backgrounds. Further improvements can be derived using fluorescent molecules with a higher ratio of fluorescent quantum efficiency to molar extinction coefficient then NADH; examples include Methulumbelliferone, Orthopthaldehyde, fluorescamine, and fluoroscein.

EXAMPLE III

The above Glucose system provides an example of a reagent system which produces relatively large but still substantially optically thin concentrations of NADH. The following example illustrates an assay of blood serum for glutamate-oxalacetate transaminase (GOT) in which the relative changes in NADH concentration during the reaction are much smaller, and in which the reaction converts the fluorescent NADH to the non-fluorescent NAD according to the following reaction scheme

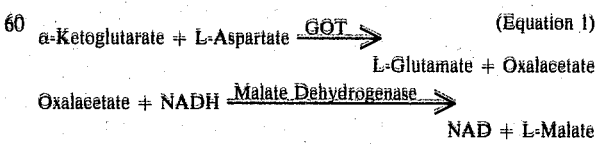

A GOT-analyzing reagent system according to the invention for deposition on reaction sites has the following constituent concentrations.

TABLE III

| Constituent | Concentration |
| --- | --- |
| ph 7.4 Phosphate Buffer | 0.20 moles/liter |
| L-Asparate | 0.144 moles/liter |
| α-Ketoglutarate | 0.026 moles/liter |
| Malate dehydrogenase | 1332 IU/liter |
| Lactate dehydrogenase | 1332 IU/liter |
| Polyox resin | 10 mg/ml |
| Brij-35 | 0.03% (W/V) |

This can be prepared using the SGOT kit available under the trade designation stat-Pack from Calbiochem, 10933 N. Torrey Pines Road, LaJolla, California 92037. Vial A of that kit is reconstituted with 3.9 ml of the 1% polyox solution containing 0.1% (V/V) of the Brij-35 solution. The resulting reagent is four times as concentrated as for standard usage according to the Calbiochem directions.

Reaction sites are prepared by the deposition of twenty microliters of this reagent system on Whatman #3 paper, with subsequent drying to constant weight under vacuum. The mixture contains all necessary components except the NADH, which is added separately as described below.

EXAMPLE IIIA

The assay is run by diluting the sample of blood serum 1:10 in buffered diluent containing the missing NADH, and depositing seventeen microliters of the dilution on the previously prepared reaction site. The decrease in fluorescence is then monitored.

The diluent composition is:

TABLE IV

| Constituent | Concentration | Source |
| --- | --- | --- |
| ph 7.8 Ultra Tris Buffer | 0.05 moles/liter | Leon Labs lot #611015 |
| NADH | 0.08 moles/liter | Calbiochem Stat Pak, Vial B |
| glycerol | 1% | Mallinckrodt #5091 |
| Lactate deyhydrogenase | 600 IU/liter | Sigma L-1254 |
| Brij-35 | 0.02% (W/V) | Sigma #430 AG6 |

LDH is used in the assay to minimize interferences produced by endogenous serum constituents which vary from sample to sample. The LDH in the diluent is prepared by adding 2.9 ml of 50% glycerol to the Sigma vial (which contains LDH in 50% glycerol), diluting the resulting solution 1:1000 in 50% glycerol and adding 0.1 ml to 4.9 ml of the NADH solution.

To stabilize fluorescence drift of the monitored reaction, it has been convenient to use a partially reflecting backing made of polished stainless steel. In the instrument of FIGS. 1 and 2, this backing is the recessed surface 24. Its reflectance relative to a highly polished aluminum surface has been estimated as approximately 40% by comparison of the increase each provides in the background fluorescence level over that of a black backing.

Figure 4A:
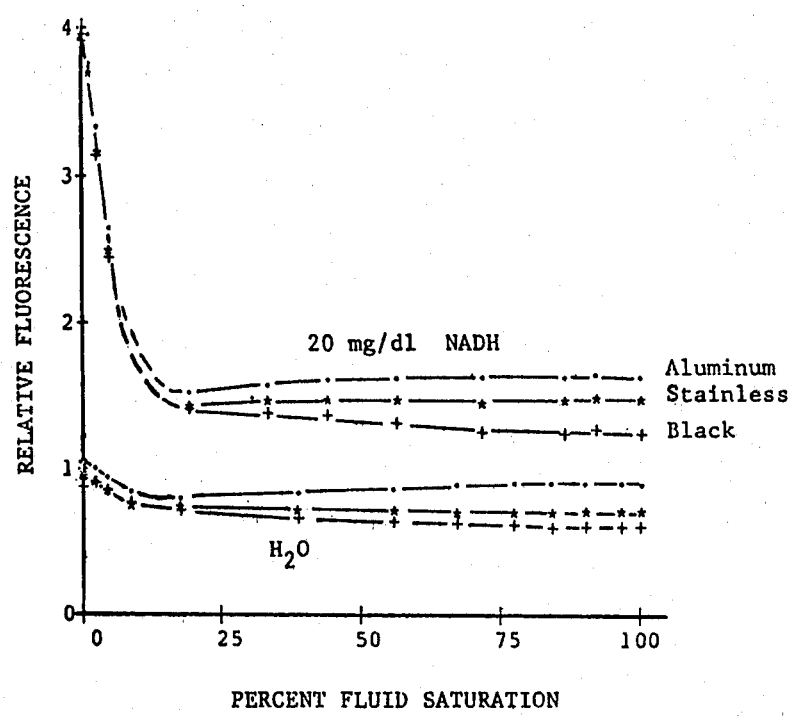
FIGS. 4 through 8 are graphs of fluorescence signal showing results realized with selected practices of the invention.
Figure 4B:
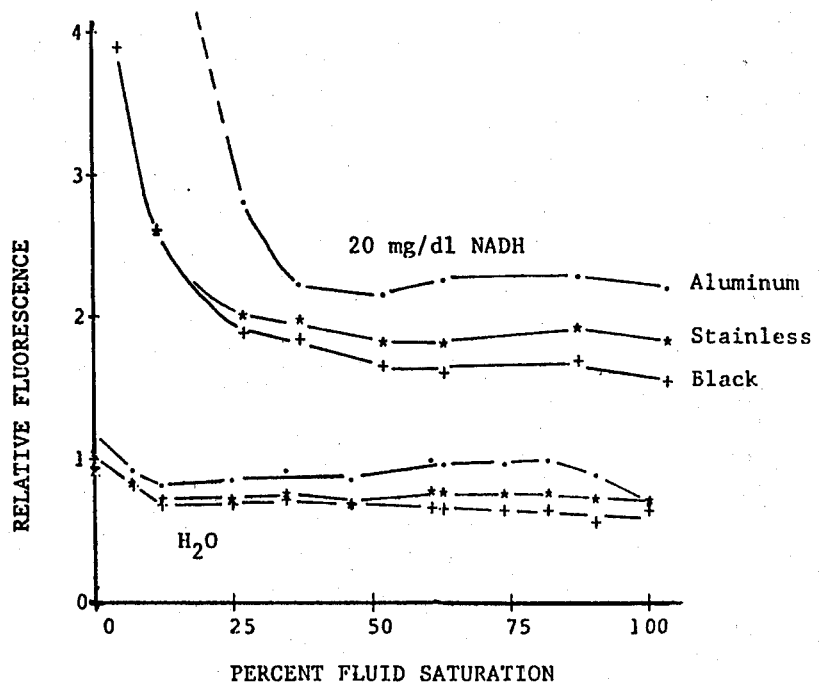

FIGS. 4A and 4B show the effect of the three backings on the sensitivity of the fluorescence level to wetness. The data in both FIGURES were measured on Whatman #3 paper; in FIG. 4A the paper was untreated whereas in FIG. 4B it was treated with the polyox conditioning agent. The polyox data show higher response to NADH, particularly at lower wetness. The plotted data is normalized to have a relative fluorescence of unity represent the background fluorescence of the initial dry medium. The background level of the Whatman #3 paper is the same with and without the polyox; this level is one-half that of 903-C paper. The data show that the intermediate backing can give a broad range for stable operation. The bright aluminum backing gives an apparent decrease in signal as the discs begin to dry because the medium becomes less transparent, with less light emerging to be reflected by the backing. With thinner media, a smaller reflectance is required to achieve the desired stability.

Viewed in this context, the role of the polyox, albumin or other thickening element in the conditioning agent is to facilitate attaining a selected wetness in the reaction site during the measuring time. The selected operating range of wetness provides maximum stability of the effective optical pathlength and of the background fluorescence signal for the assay. This role of the thickening element is supported by measurements that demonstrate analyses are best performed where results are less sensitive to wetness.

The desired effect is achieved in other assay systems as well by adjusting the total solids content of the reagent as it is applied to the reaction sites so that the diameter of the translucent area after fluid deposition is roughly 15% smaller (typical range 10%-20%) than for the untreated paper. Similar decreases in spot size and/or increases in local fluid density are observed on other media as well, such as on glass fiber papers (Whatman GFA and GFC), microcrystalline cellulose TLC plates (Avicel Uniplate brand available from Analtech, Inc.), diatomaceous earth layers (pre-adsorbant layer on Quantum Industries LQ TLC plates), and cellulose acetate electrophoresis emmbranes (Instrumentation Laboratories). By contrast, there is only a slight decrease in spot size for silica gel TLC media or the instant TLC media available from the Gelman Instrument Co. under the designation ITLC SA.

Figure 5:
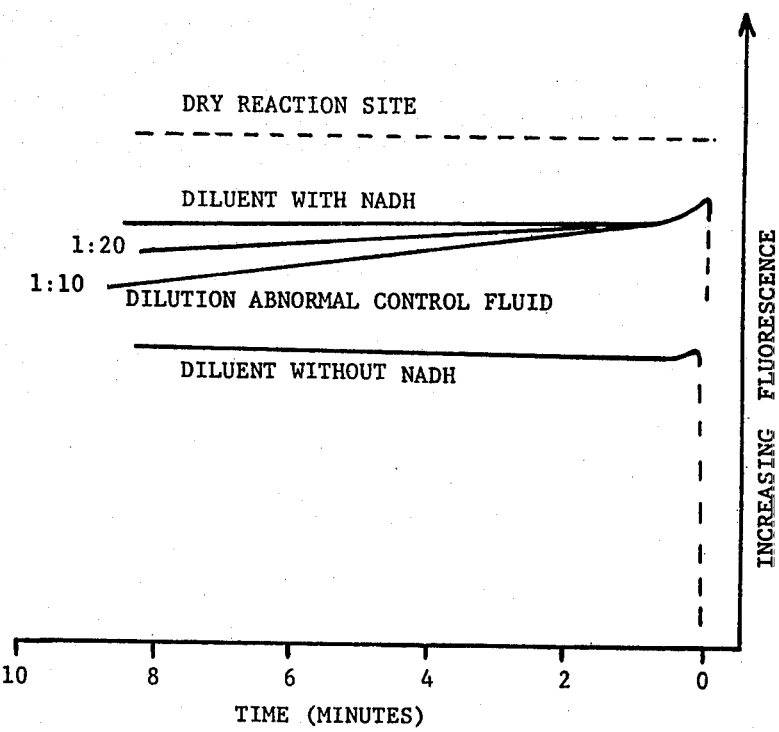

FIG. 5 shows the gross behavior of the fluorescence level as the SGOT reactions proceed. The changes, as graphed, which results from the reaction are much smaller than for the Glucose system of Example I. Note also that the fluorescence level falls rapidly at first as the NADH in the diluted specimen spreads beyond the monitored area.

The fluorometer used for these measurements employs temperature control at 30° C. as the referenced patent described with reference to FIGS. 6 and 7. Consequently, the fluorescence also decreases as the reaction mixture equilibrates to the 30° C. temperature of the window and the backing plate. The change in temperature from an environmental level at 25° C. to 30° C. produces a measurable decrease in response both for the background and for the NADH. The temperature control maintains 30° C. to better than ±0.1° C. This temperature dependence is comparable in magnitude and opposite in direction to the well known increase in reaction rate of the enzyme reagent systems, so that the two effects partially compensate. However, sensible error budgeting suggests that the NADH concentration (e.g. the total fluorescence level) be kept to a minimal level so that its fluctuations with temperature are a small fraction of the changes produced by the reaction.

Figure 6:
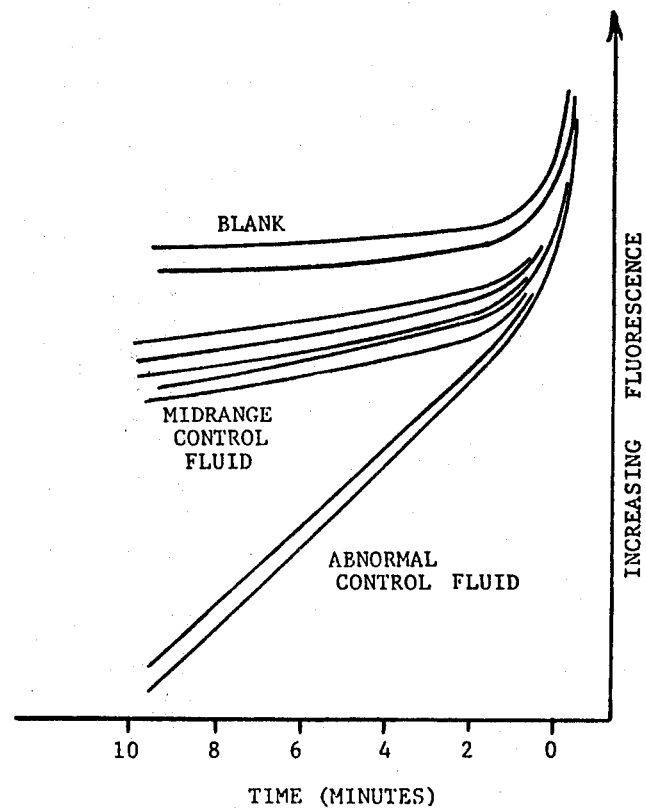
Figure 7:
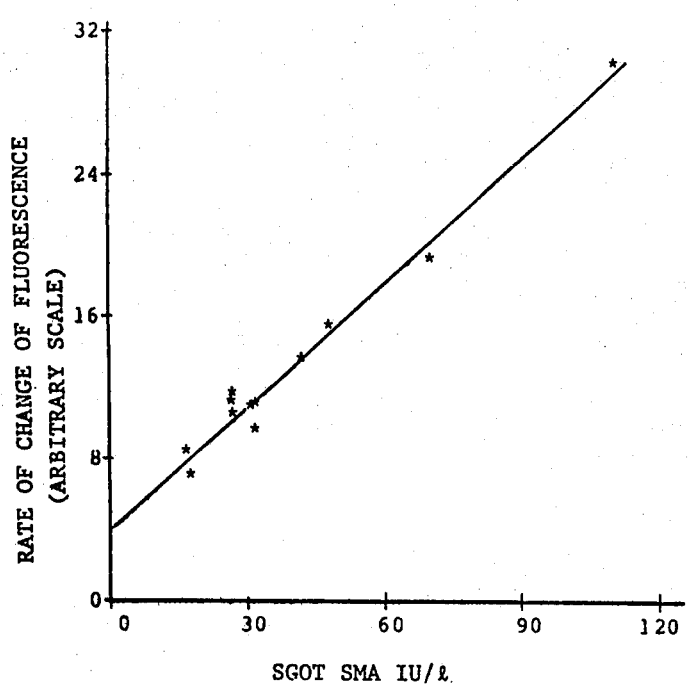

FIG. 6 plots the fluorescence signal variation of several different levels of GOT (on an expanded scale) and of several replicates at a midrange level. Using pure GOT at this level, a coefficient of variation of five percent was observed for seven replicates. FIG. 7 presents the results of a comparison study with an established routine procedure for twelve patient specimens. The correlation coefficient of the graphed data was 0.988.

EXAMPLE IIIB

FIG. 5 shows a relatively large initial decrease of fluorescence signal as the diluent which carries NADH spreads across the reaction site. It has been found that the results for any assay (of which Glucose and GOT are typical) are influenced by the rate of application of the diluted specimen. If the dilution is added too rapidly, the central area attains a relatively higher degree of wetness which gradually equalizes across the spot. If it is added too slowly, the solution enters the medium through a small central area and chromatographic ringing is heightened. Experience has shown that better repeatability results when the dilution is applied at a rate which maintains a slight visible pool of liquid on the spot beneath the pipet tip. The pool typically has a diameter of 2-3 mm. In practice this involves deposition of 10-20 microliters of solution in times of the order of one second.

As described above, it was found that sensitivity to delivery rate could be minimized conveniently by the use of an intermediate pad or disc punched from a thin sheet of porous hydrophilic polyethylene or from a sheet of the 903-C or Whatman #3 papers. The disc diameter approximates that of the visible pool noted above; disc diameters from 1.5 mm to at least 3 mm have been successful. The disc serves as a focus for pooling and as a reservoir to support the excess fluid until the reagent-laden site draws it off.

In operation, such wicking discs were placed on the center of the site and the solution pipeted into the disc, as FIG. 3 shows. After the solution was added, the disc was removed and the reaction site examined with the fluorometer. Results obtained were equivalent to those of FIG. 5 and FIG. 6. The wicking discs are equally useful in other assays.

The use of NADH as a component of the diluent can be inconvenient. As an alternative, wicking discs were dipped in the NADH-containing diluent of Table IV and dried to constant weight under vacuum. The sample was then diluted in buffer alone, and applied to the reaction sites through these NADH-containing discs. The concentration of NADH in the diluent was adjusted for each type of disc to give the same increment in fluorescence and flatness of the blank as shown in FIGS. 5 and 6. The preferred discs were punched from a continuous sheet of porous polyethylene (Bolab Corp. hydrophilic HDPE 35 micron pore size, 1/16 inch thick, 150 inch in diameter) and gave equivalent results when dipped in the diluent of Example IIIA. The same volume of diluted sample was used as in Example IIIA.

Similarly good results were obtainn for the Glucose System by grinding up an Eskalab tablet and compressing a small amount of the resultant powder into a small tablet at the center of a reaction site. The diluted sample was then added to the site, eluting reagent from the compressed powder as it entered the site.

EXAMPLE IIIC

As another alternative to the use of NADH in the diluent, a zoned reagent site was prepared by adding the NADH to sites previously prepared as in Example IIIA. The NADH was in the diluent of Table IV but prepared with ten times elevated NADH concentration as in Example IIIA; a small volume, e.g. three microliters, was applied as an overspot at the center of the previously prepared site. The sites were then dried for a second time under vacuum. The three microliter volume was chosen to correspond approximately to the diameter of the preferred liquid pool which forms as the diluted specimen is added.

Figure 8:
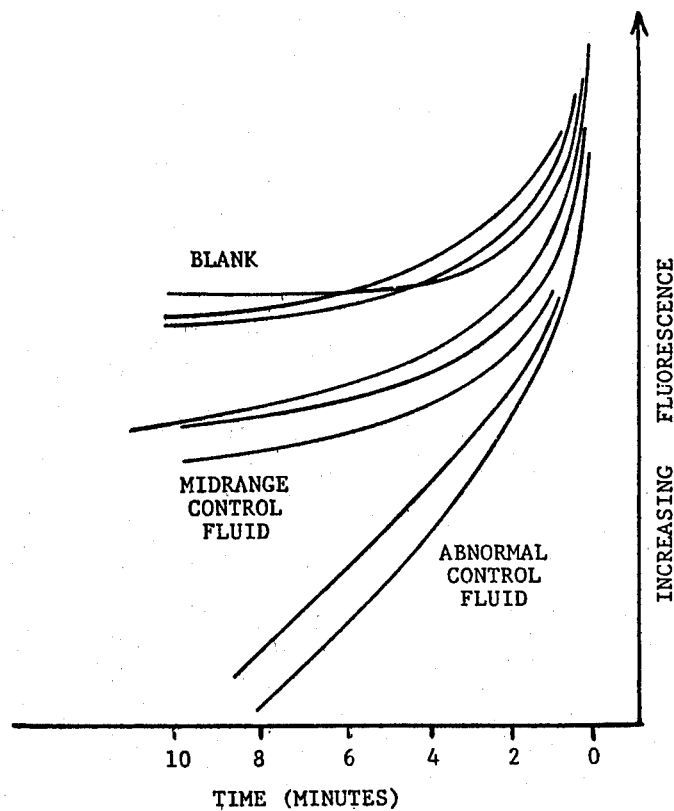

The assay was run by depositing on the center of the zoned site seventeen microliters of the serum sample diluted 1/10 in the diluent of Example IIIA but containing no NADH. FIG. 8 shows (with the same scale as FIG. 6) the fluorescent signal which results when samples of various concentration are added. The sensitivity is comparable to Example IIIA, but the results are more variable and show steeper slopes at early times.

If larger volumes are used for the NADH overspot, or if the complete reagent including NADH is used in the initial preparation of the sites, the initial slope is still greater and persists longer so that it is difficult to obtain a linear portion suitable for measurement. This is understood to occur under these conditions because the NADH forms an extremely "ringed" spot within the instrument field of view.

The reagent systems described above and in the referenced patent have relative concentrations of components which differ significantly from their usual relationship as optimized for conventional use in liquid solution. Generally the high molecular weight reagents, e.g. enzymes, are found at higher concentration than for such conventional in-vitro use. The low molecular weight, more diffusible components are present at still higher concentration. Typically the enrichment ratio for low molecular weight moelcules is two to four times higher than for the high molecular weight components. The latter is typically three to five times concentrated, and may range in extreme cases as high as twenty times.

It is believed that the active enzyme reagents and any other high molecular weight constituents are to be concentrated more than for conventional practice in order to overcome an effective diffusion barrier which results in a porous medium from the unsaturated condition of the reaction site and/or the relatively larger (vis-a-vis in-vitro) surface area of the interface of the liquid with the solution-supporting surfaces. At the same time, the diffusible, low molecular weight, components are relatively more concentrated in order that they come to equilibrium, after the differential chromatographic separation produced by the addition of diluted specimen, at values which are then optimal.

The NADH concentration set forth above for the SGOT assay is a notable exception in that it has been kept low to minimize the contribution of drifts in temperature and wetness on the overall assay error. For this case the reaction kinetics are such that the rate is not sensitive to the exact NADH concentration, and only the upper limit of linearity is affected (e.g. the system runs linearly until the NADH in the reaction mixture is exhausted).

By way of further example, the above-noted glucose reagent system runs to completion extremely rapidly if it is used in a conventional liquid solution, due to the high enzyme concentrations. It has been found that the maximum rates of change produced in optimized enzyme assays performed on porous media as set forth herein can approach the corresponding maximum rates for the same reagents optimized for in-vitro use, when the rate is expressed in moles of substrate converted per unit of time and of volume, but only at the elevated concentration described.

It is further believed that conditioning agent is advantageous because it increases the isolation of the enzymes from the medium structure, and offsets configurational changes of the enzyme molecule induced by the proximity of so much surface within the medium. Along these lines, it has been observed that the optimized maximum rate for enzymatic reactions increases as the concentration of conditioning agent, and the wetness, increase.

In summary, the improvements and features of this invention are described above with reference to a photometric instrument that positions a reaction site at a selected location in a photometer field of view in highly repeatable fashion and with operator ease. This repeatable and accurate site-locating capability, together with the selected recessing of instrument optical surfaces from the reaction site, provide maximal uniformity in the optical coupling of successively-tested sites with the measuring optics of the instrument. The desirability of an intermediate reflectance on the recessed surface in attaining this objective is also set forth.

Further, the reaction sites are of a fibrous or other porous medium that preferably is pretreated with a wetness-enhancing conditioning agent. The agent can be applied in advance of reagents, but is more conveniently applied as part of a reagent pre-treatment of the medium.

The practice of the invention includes delivering liquid to a pretreated reaction site through a porous disc or other wicking element to control the liquid delivery to a rate-limited but continuous application at the central portion of the site. The wicking element facilitates attaining at the point of liquid application a pool-like body of liquid similar to that which occurs naturally when liquid is applied at the correct rate without a wicking element. A preferred wicking disc accordingly has a diameter of 1.5 to 2 millimeters, although other sizes within approximately a 1 to 3 millimeter range can be used.

Chemical analysis with the techniques set forth can be monitored as a two-point or other rate measurement during the reaction of interest. It can also be carried out, especially where the monitored signal is sufficiently large relative to nonuniform and other nonrepeatable background signals, with an end point measurement. This measure can, in some instances, be made after the reaction site has dried.

Chemical spot test analysis in accordance with the invention employs conventional analytical reactions. Accordingly, the constituents of reagent systems for practicing the invention can be conventional, but as set forth above the concentrations are significantly higher.

It will thus be seen that the objects set forth above, among those made apparent from the preceding description, are efficiently attained and, since certain changes may be made in carrying out the above methods and in the constructions, compositions and articles set forth without departing from the scope of the invention, it is intended that all matter contained in the above description or shown in the accompanying drawings shall be interpreted as illustrative and not in a limiting sense.

It is also to be understood that the following claims are intended to cover generic and specific features of the invention herein described, and statements of the scope of the invention which, as a matter of language, might be said to fall therebetween.

Having described the invention, what is claimed as new and secured by Letters Patent is:

1. A method for preparing a porous medium for use in chemical spot test analysis employing a measured parameter responsive to concentration of a reaction-produced material at a test site on the porous medium, said method including the improvement comprising the step of exposing at least said test site of said medium to a liquid preparation conditioning agent having a balance of hydrophobic and hydrophilic properties for retarding the spreading of liquid in the medium and for increasing the concentration of liquid the medium can hold, said exposure being sufficient, after drying, to diminish the absorption of liquid by the porous structure of said medium.

2. A method as defined in claim 1, comprising the further improvement comprising the step of introducing reaction-producing reagents to said test site together with said liquid preparation of conditioning agent.

3. A method as defined in claim 1, comprising the further improvement in which said conditioning agent includes a thickening element and a surfactant.

4. A method as defined in claim 1, comprising the further improvement in which said conditioning agent includes a thickening ingredient selected from the group consisting of a high molecular weight crystalline, ethylene oxide polymer, albumin, gum arabic, guar gum, and mannitol.

5. A method as defined in claim 1, comprising the further improvement in which said conditioning agent is a low molecular weight polyol surfactant of selected hydrophobic and hydrophilic characters.

6. A porous medium for use in measuring a selected product of chemical reactants at a test site on the medium with means for subjecting the site to oscillating electromagnetic energy and for sensing a selected parameter of energy which is responsive to the oscillating energy and to the presence of the selected reaction product, said medium having the improvement comprising a conditioning agent in at least the test site of the medium, said conditioning agent being present from exposure of the medium to a solution of said agent and subsequent drying, said agent having hydrophobic and hydrophilic properties selected for retarding the spread of liquid in the medium and for increasing the concentration of liquid the medium can hold.

7. A medium as defined in claim 6 in which said conditioning agent includes a thickening element and a surfactant.

8. A medium as defined in claim 6 in which said conditioning agent includes a thickening element selected from the group consisting of high molecular weight crystalline, ethylene oxide polymer, albumin, gum arabic, guar gum, and mannitol.

9. A medium as defined in claim 6 in which said conditioning agent is a low molecular weight polyol surfactant of selected hydrophilic and selected hydrophobic characters.

10. In a porous medium having a test site for bearing chemical reactants which produce a reaction product measurable upon being subjected to oscillating electromagnetic energy, a parameter of which is responsive to the presence of the selected reaction product and is sensed for measurement, said porous medium having a substantially uniform structure within and contiguously beyond the test site, the improvement comprising a wick overlying a fragmentary central portion of the test site for receiving liquid and for controlling the rate of delivery to the test site of such liquid.

11. In a porous medium according to claim 10, the further improvement wherein said wick is a disc-like member.

12. In a porous medium according to claim 10, the further improvement wherein said wick comprises a cylindrical disc-like element having a diameter substantially between one millimeter and three millimeters.

13. In a porous medium according to claim 10, the further improvement wherein said wick is a cylindrical disc-like member having a diameter substantially in the order of one to two millimeters.

14. In a porous medium according to claim 10, the further improvement comprising a chemical reagent carried on said wick for transfer therefrom to said porous medium upon the flowing of liquid through the wick.

15. Apparatus according to claim 10 further comprising a reagent carried on said wick element for transfer therefrom to said medium upon the flowing of liquid through the wick element.

* * * * *